(12) United States Patent
Abraham et al.

(10) Patent No.: US 10,809,233 B2
(45) Date of Patent: Oct. 20, 2020

(54) BACKING COMPONENT IN ULTRASOUND PROBE

(71) Applicant: GENERAL ELECTRIC COMPANY, Schenectady, NY (US)

(72) Inventors: Jessica Lynn Abraham, Chandler, AZ (US); Jimmie Autrey Beacham, West Allis, WI (US); Scott William Easterbrook, Bainbridge Island, WA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 182 days.

(21) Appl. No.: 15/840,806

(22) Filed: Dec. 13, 2017

(65) Prior Publication Data
US 2019/0178849 A1    Jun. 13, 2019

(51) Int. Cl.
*B29C 64/165*    (2017.01)
*B33Y 10/00*    (2015.01)
(Continued)

(52) U.S. Cl.
CPC .......... *G01N 29/24* (2013.01); *A61B 8/4483* (2013.01); *B29C 64/165* (2017.08); *B33Y 10/00* (2014.12);
(Continued)

(58) Field of Classification Search
CPC .... A61B 8/4483; G10K 11/002; G01N 29/24; G01N 29/221; B29C 64/165;
(Continued)

(56) References Cited

U.S. PATENT DOCUMENTS

| 4,800,316 | A |   | 1/1989 | Ju-Zhen |
| 5,810,009 | A | * | 9/1998 | Mine ............... B06B 1/0622 310/334 |

(Continued)

FOREIGN PATENT DOCUMENTS

| EP | 2992829 A1 | 3/2016 |
| JP | 2009071393 A | 4/2009 |
| JP | 2015043810 A | 3/2015 |

OTHER PUBLICATIONS

European Search Report dated May 17, 2019; 7 pages.
(Continued)

*Primary Examiner* — Jacques M Saint Surin
(74) *Attorney, Agent, or Firm* — Grogan, Tuccillo & Vanderleen, LLP (57) ABSTRACT

A backing component configured to receive and attenuate transmitted acoustic signals from a transducer element in an ultrasound probe is disclosed. The backing component has a unitary structure of a first material and a second material, and a variation in packing density of the first material across at least a portion of a thickness of the backing component. Further, a method of making a backing component for a transducer element in an ultrasound probe is disclosed. The method includes performing an additive manufacturing technique using a first material and a second material to form the backing component that has a unitary structure of the first material and the second material. Performing the additive manufacturing technique involves varying a packing density of the first material across at least a portion of thickness of the backing component.

18 Claims, 4 Drawing Sheets

(51) Int. Cl.
   *B33Y 80/00* (2015.01)
   *G01D 11/10* (2006.01)
   *G01N 29/22* (2006.01)
   *G10K 11/00* (2006.01)
   *G01N 29/24* (2006.01)
   *A61B 8/00* (2006.01)
   *B29K 63/00* (2006.01)
   *B29K 103/06* (2006.01)

(52) U.S. Cl.
   CPC .............. *B33Y 80/00* (2014.12); *G01D 11/10* (2013.01); *G01N 29/221* (2013.01); *G10K 11/002* (2013.01); *B29K 2063/00* (2013.01); *B29K 2103/06* (2013.01); *B29K 2995/0002* (2013.01)

(58) Field of Classification Search
   CPC ........ B33Y 10/00; B33Y 80/00; G01D 11/10; B29K 2995/0002; B29K 2063/00; B29K 2103/06
   USPC ............................................................ 73/642
   See application file for complete search history.

(56) References Cited

U.S. PATENT DOCUMENTS

| | | |
|---|---|---|
| 6,036,777 A | 3/2000 | Sachs |
| 6,831,394 B2 | 12/2004 | Baumgartner et al. |
| 9,089,875 B2 | 7/2015 | Gil-Ju et al. |
| 9,237,880 B2 | 1/2016 | Davidsen et al. |
| 2005/0127793 A1 | 6/2005 | Baumgartner et al. |
| 2006/0043839 A1 | 3/2006 | Wildes et al. |
| 2011/0121687 A1* | 5/2011 | Aoki ...................... B06B 1/0677 310/334 |
| 2012/0007471 A1 | 1/2012 | Tai |
| 2012/0181902 A1* | 7/2012 | Gelly ................... G10K 11/004 310/341 |
| 2012/0238880 A1 | 9/2012 | Davidsen |
| 2013/0088122 A1 | 4/2013 | Krohn et al. |
| 2013/0197368 A1* | 8/2013 | Jin ....................... G10K 11/002 600/459 |
| 2013/0345567 A1 | 12/2013 | Sudol et al. |
| 2014/0249419 A1 | 9/2014 | Morita |
| 2014/0373619 A1* | 12/2014 | Slay ...................... E21B 47/14 73/152.58 |
| 2016/0151840 A1 | 6/2016 | McCoy et al. |
| 2016/0185056 A1 | 6/2016 | Beacham et al. |
| 2016/0368054 A1 | 12/2016 | Ng et al. |
| 2017/0135673 A1 | 5/2017 | Bruestle |

OTHER PUBLICATIONS

Low G C et al: "Design and construction of short pulse ultrasonic probes for non-destructive testing", Ultrasonics, IPC Science and Technology Press Ltd. Guildford, GB, vol. 22, No. 2, Mar. 1, 1984 (Mar. 1, 1984), pp. 85-95, XP025824264, ISSN: 0041-624X, DOI: 10.1016/0041-624X(84)90026-X [retrieved on Mar. 1, 1984].

* cited by examiner

BACKING COMPONENT IN ULTRASOUND PROBE

BACKGROUND

Embodiments of the disclosure generally relate to a backing component for a transducer element in an ultrasound probe. More particularly, embodiments of the disclosure relate to a backing component having a unitary structure and method for manufacturing the backing component using additive manufacturing techniques.

There are various technical requirements of a backing component for an ultrasonic transducer element of an ultrasound probe. According to one requirement, it may be desirable to prevent or minimize the reflection of acoustic signals by the backing component or a back surface of the backing component. Further, it may be desirable that the backing component participates in damping the undesired sound reverberation created by the ultrasonic transducer element to control the pulse duration of the ultrasonic signal outgoing from the ultrasonic transducer element for imaging process.

Therefore, it may be desirable to have a backing component that has a variable attenuation material property in the Z-axis of the backing component. Conventional techniques for forming multiple attenuation zones in a backing component, often result in boundary layer effect resulting in poor image quality. Therefore, it may be desirable to design a backing component that has a variable attenuation material property in the Z-axis of the backing component, with minimal or no boundary layer effect, and further devise a method for fabricating such a backing component.

BRIEF DESCRIPTION

In accordance with some aspects, a backing component configured to receive and attenuate transmitted acoustic signals from a transducer element in an ultrasound probe is disclosed. The backing component has a unitary structure of a first material and a second material, and a variation in packing density of the first material across at least a portion of a thickness of the backing component.

In accordance with some aspects, an ultrasound probe having an acoustic lens, an acoustic matching layer, a transducer element, and a backing component is disclosed. The backing component has a unitary structure of a first material and a second material, and a variation in packing density of the first material across at least a portion of a thickness of the backing component.

In accordance with some aspects, a method of making a backing component for a transducer element in an ultrasound probe is disclosed. The method includes performing an additive manufacturing technique using a first material and a second material to form the backing component that has a unitary structure of the first material and the second material. Performing the additive manufacturing technique involves varying a packing density of the first material across at least a portion of thickness of the backing component.

DRAWINGS

These and other features and aspects of embodiments of the present disclosure will become better understood when the following detailed description is read with reference to the accompanying drawings in which like characters represent like parts throughout the drawings.

DETAILED DESCRIPTION

As used herein, an element or step recited in the singular and proceeded with the word "a" or "an" should be understood as not excluding plural elements or steps, unless such exclusion is explicitly recited. As used herein, the term "or" is not meant to be exclusive and refers to at least one of the referenced components being present and includes instances in which a combination of the referenced components may be present, unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. In some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

To more clearly and concisely describe and point out the subject matter, the following definitions are provided for specific terms, which are used throughout the following description and the appended claims, unless specifically denoted otherwise with respect to particular embodiments. As used herein, a "unitary structure" is a monolithic structure that does not have any joined parts or layers. A "packing density of the first material in a region" is a ratio of the volume occupied by the first material in the region to the total volume of the region. "A variation in packing density of the first material across a thickness" is an increase or decrease in the packing density across the thickness. The "Z-axis" or "Z-axis direction" of the ultrasound probe is the direction in which the ultrasound waves travel, inside the ultrasound probe. A "thickness" of the backing component is the depth of the backing material in the Z-axis direction of the ultrasound probe starting from the transducer element. A "build layer" is a portion of a component that is built during one step of the manufacturing process.

Figure 1:
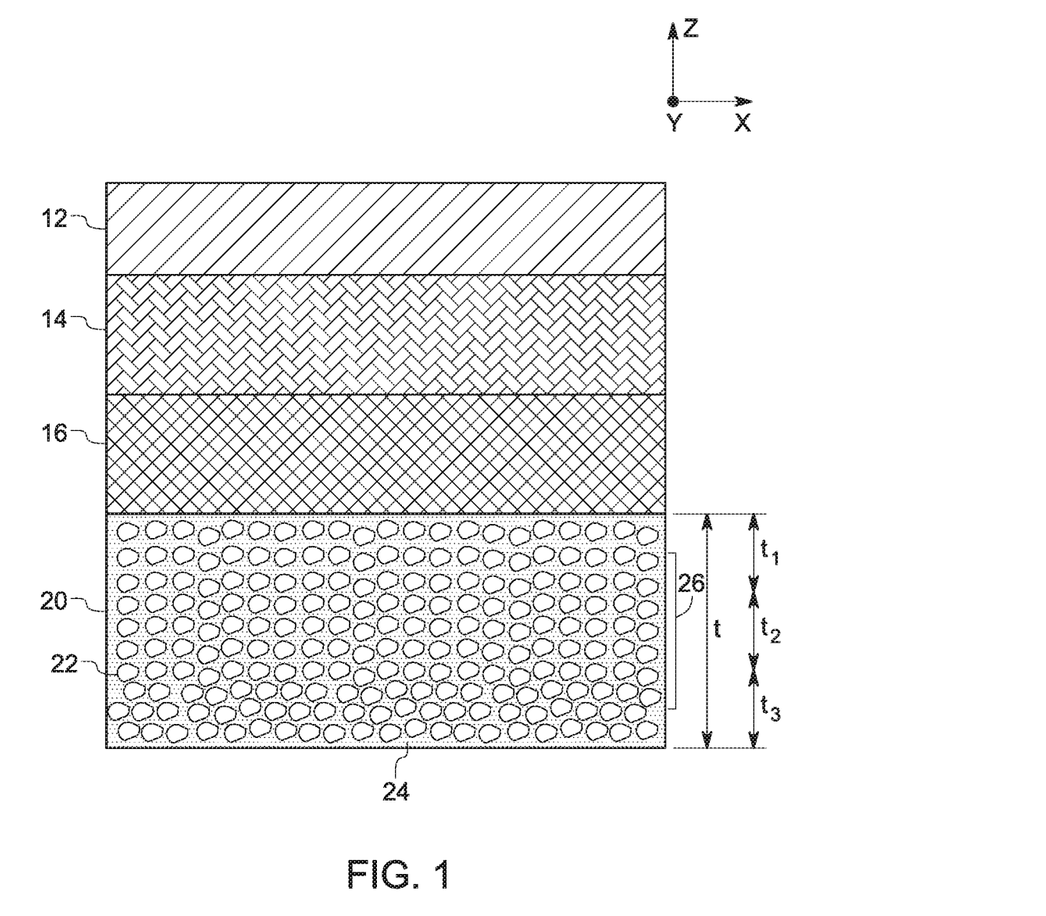
FIG. 1 is a schematic cross-sectional view of an ultrasound probe, in accordance with some embodiments of the present disclosure.

FIG. 1 depicts a cross-sectional view of an ultrasound probe 10, in accordance with embodiments of the present disclosure. Ultrasound probe 10 includes an acoustic lens 12, an acoustic matching layer 14, a transducer element 16, and a backing component 20. The acoustic matching layer 14 may have multiple layers in some embodiments. The ultrasound probe 10 may further include electrical elements for connection to an ultrasound system.

The transducer element 16 can convert electrical signals into ultrasound waves to be transmitted toward a target and can also convert received ultrasound waves into electrical signals. Ultrasound waves are transmitted from and received by the ultrasound probe 10. The received ultrasound waves can be used by an ultrasound system (not shown in FIG. 1) to create an image of the target.

The backing component 20 of the ultrasound probe 10 is configured to receive and attenuate transmitted acoustic signals from the transducer element 16. The backing component 20 has a unitary structure and includes a first material 22 and a second material 24.

The first material 22 and the second material 24 are different from each other. In some embodiments, the first material 22 and the second material 24 of the backing component 20 may be chosen such that one of them is an acoustic scatterer and another one is an acoustic absorbing material. This combination of acoustic scatterer and acoustic absorbing materials aid in acoustic impedance and attenuation of the ultrasound waves. In some embodiments, the first material 22 or the second material 24 of the backing component 20 may also function as a thermal filler to increase thermal conductivity.

In some embodiments, the first material 22 may include high density materials such as, elemental metals, alloys, high thermally conductive ceramic particles, or combinations thereof. Non-limiting examples of the first material 22 includes tungsten, tantalum, tungsten carbide, tantalum carbide, tungsten silicide, or combinations thereof. In some embodiments, the first material 22 may be a mixture of two or more materials.

In some embodiments, the first material 22 is in the form of particles having a median particle size greater than 10 micrometers and less than 50 micrometers. In some embodiments, the median particle size of the first material is in a range from about 15 micrometers to about 30 micrometers. In certain embodiments, the particles of the first material 22 has a monomial particle size distribution throughout the unitary structure of the backing component 20.

In some embodiments, the first material 22 is in the form of particles bonded by the second material 24. In some embodiments, the second material 24 may include low density materials such as, low density elemental metals, polymers, or a combination thereof. In some embodiments, the first material includes a metal material and the second material includes a polymer material. In some embodiments, the second material 24 may be present in a continuous form, substantially wetting the first material 22. Non-limiting examples of the second material 24 include graphite, copper, epoxy, silicone, or combinations thereof. In certain embodiments, the second material 24 is an epoxy polymer.

In one example, the backing component 20 may include tungsten metal as the first material 22 and epoxy as the second material 24. In one example, the backing component 20 includes an epoxy filled graphite foam as the second material 24. Depending on the properties of the first material 22 and the second material 24, and further on the acoustic frequency of the ultrasound waves generated by the transducer element 16, the first material 22 and the second material 24 may be present in appropriate amount in the backing component. In some embodiments, a weight ratio of the first material 22 to the second material 24 in the backing component is in a range from about 3:1 to about 50:1.

In some embodiments, the backing component 20 may further include a matrix material (not specifically shown in FIG. 1), in addition to the first material 22 and the second material 24. In some embodiments, the matrix material may be a polymer that is different from the second material 24. In certain embodiments, the matrix material is a cured form of a binder that is used to bond the first material 22 during preparation of the backing component 20. In some embodiments, the first material 22 and the second material 24 are bonded by the matrix material, if the matrix material is present. In an example embodiment, the backing component 20 includes tungsten metal and a silicone in a matrix of an epoxy or a polyurethane.

The backing component is further characterized by a packing density of the first material 22 and the second material 24. In some embodiments, an average packing density of the first material 22 in the backing component 20 may be in an amount ranging from about 30 volume % to about 90 volume % of the backing component 20. In some embodiments, the average packing density of the first material 22 is in the range from about 40 volume % to about 80 volume % of the backing component. In some embodiments, an average packing density of the second material 24 in the backing component 20 may be in an amount ranging from about 10 volume % to about 70 volume % of the backing component 20. In some embodiments, the average packing density of the second material 24 is in the range from about 20 volume % to about 60 volume % of the backing component. A packing density of the matrix material, if present, may be less than 5 volume % of the backing component.

As noted earlier, the backing component 20 further has a variation in packing density of the first material 22 across at least a portion 26 of its thickness t. Referring again to FIG. 1, the thickness t of the backing component 20 is in a direction that the ultrasound waves travel inside the backing component. In some embodiments, the thickness t of the backing component is in the direction of the z-axis of the ultrasound probe 10, as shown in FIG. 1.

As used herein a "variation in packing density" is an increase or a decrease in packing density. Thus, a "variation in packing density of the first material across a portion 26" is an increase or a decrease in packing density of the first material 22 in the portion 26 while traversing through the portion 26 in the z-axis direction. The packing density may gradually increase across the portion 26, gradually decrease across the portion 26, or may increase and decrease alternately while traversing through the portion 26. In some embodiments, a variation in the packing density of the first material 22 across the portion 26 is such that the packing density at a given point in the portion 26 varies (i.e., increases or decreases) by an amount that is greater than 5% of the average packing density of the first material 22 in the portion 26. In some embodiments, the packing density varies by an amount that is greater than 10% of the average packing density of the first material 22 in the portion 26.

In some embodiments, the variation in packing density of the first material 22 is in the form of a step change across the at least a portion of thickness of the backing component 20. In some such embodiments, the number of step changes employed may be controlled to minimize an abrupt change in the packing density across the thickness of the backing component, and yet provide the desired packing density variation for the attenuation and impedance of the acoustic signals. In some embodiments, the number of step changes employed may be greater than 100. In some embodiments, the packing density of the first material 22 across the thickness t of backing component 20 is varied by employing more than 200 step changes. In some embodiments, each step change changes the packing density as a small fraction of the overall change in the packing density across the portion 26 of thickness t of the backing component 20. For example, if the packing density of the first material 22 in the portion 26 gradually increases from about 50 volume % to about 70 volume % through the portion 26 in the z-axis direction, then each step change may contribute to less than 0.2% of the increase. In some embodiments, each step change of the variation may contribute to less than 0.1% of the variation. In some embodiments, any reflection of the ultrasound waves brought about due to the step change in the packing density may be suppressed before reaching the transducer element 16.

In some embodiments, the variation in packing density of the first material 22 is continuous across the at least a portion 26 of thickness of the backing component 20. The variation in packing density is said to be continuous when the effect of variation in packing density across the portion 26 does not reflect the ultrasound waves emitted from the transducer element 16. A continuous variation in packing density of the first material 22 may provide a continuous and effective attenuation of the sound waves within the backing component 20. In some embodiments, the packing density of the first material 22 varies as a step change across a first portion $t_1$ of the thickness t and changes continuously across a second portion $t_2$ of the thickness of the of the thickness t in the backing component 20.

In addition to the variation in packing density of the first material 22, the backing component 20 may further have a variation in packing density of the second material 24 across the at least a portion of the thickness of the backing component 20. While the variations in the packing densities of the first material 22 and the second material 24 are discussed herein with reference to the z-axis of the backing component, the packing densities of the first material 22 and the second material 24 may also vary in the X-Y plane of the backing component 20. In certain embodiments, the packing densities of the first material 22 and the second material 24 are controlled in the z-axis without resulting in notable variation in packing densities of the first material 22 and the second material 24 in the X-Y plane of the backing component 20.

The variation in the packing density of the first material 22 across the thickness may further be specifically controlled to enhance the attenuation and impedance of the ultrasound waves in the backing component 20. For example, in some embodiments, the packing density of the first material 22 increases across a first portion $t_1$ of the thickness t of the backing component 20 and decreases across a second portion $t_2$ of the thickness t of the backing component 20, instead of continuously increasing or decreasing across the thickness t of the backing component 20. In some embodiments, the packing density of the first material 22 increases in the first portion $t_1$ of the thickness t (FIG. 1), decreases in the second portion $t_2$ of the thickness t and again increases in the third portion $t_3$ of the thickness t, as measured in the z-axis within the backing component 20 when measured from the transducer element 16. The thicknesses $t_1$, $t_2$, and $t_3$ need not have the same dimensions. In some embodiments, the packing density of the first material 22 may have at least two iterations of alternate increase and decrease across the thickness t of the backing component 20. That is, the packing density of the first material 22 may increase and decrease at least twice across the thickness of the backing component 20. This kind of increase and decrease in packing densities of the first material 22 may, in effect reduces the overall increase or decrease of the packing densities of the packing densities when measured across the entire thickness of the backing component 20, thus maintaining the average packing density of first material 22 to a desired value. For example, in an embodiment, where the packing density of the first material 22 increases over a first portion $t_1$ of the thickness, decreases over a second portion $t_2$ of the thickness, and again increases over a third portion $t_3$ of the thickness, the overall variation in packing density of the first material 22 across the entire thickness t spanning the first, second, and third portions may be less than the variation in packing densities across the individual first, second, and third portions of thickness.

In some embodiments, variation in packing densities of the first material 22 and the second material 24 across at least a portion 26 of the thickness t of the backing component 20 results in variation in overall density of the backing component as measured by mass by volume ratio of that portion of the backing component 20. In general, a high acoustic impedance Z is required for damping the vibration of the transducer element and to create the correct pulse shape and frequency spectra for imaging process. The acoustic impedance Z is given by a product of density, ρ and longitudinal wave speed-of-sound in the backing component 20, given by the equation $$Z = \rho \cdot v \qquad (1)$$

Therefore, in general, it may be desirable that the backing component 20 has a high density and low porosity. In some embodiments, a density of the backing component may be greater than 5 g/cc. Further, maintaining a high density of the backing component, along with desired variation of packing density of the first material 22 in the backing component is advantageous for high acoustic impedance of the backing component. In some embodiments, the porosity of the backing component 20 is less than 5 volume % of the backing component. In some embodiments, the backing component has less than 0.5 volume % porosity.

A variation in packing density of the first material 22 may provide a variable attenuation property in the Z-axis direction of the backing component 20, and further control the impedance of the acoustic signals travelling in the backing component 20. The variation in packing density of the first material 22 across a thickness t of the backing component 20 may result in variation in density of the backing component 20 encountered by the ultrasound waves in the thickness t direction and may aid in uniquely controlling the gradient of attenuation within the single piece of backing component 20. Varying the packing density of the first material 22 in the backing component aids in varying density of the backing component without the need for varying the type of material present in the backing component across the thickness direction and without producing undesired reflection of the ultrasound waves in the backing component 20. This may advantageously provide for enhanced image quality and specificity of the ultrasound probe 10, as compared to an ultrasound probe that has laminated layers of different backing material in the backing component. A backing component having laminated layers may have limitations of control on tuning the stack for optimal image quality and attenuation performance.

Furthermore, the unitary structure of the backing component 20 may be particularly advantageous in reducing reflection of the ultrasound waves back to the transducer element 16. For example, if the backing component includes multiple layers in the direction of travel of the ultrasound waves from the transducer element 16, boundaries of the layers may reflect some part of the ultrasound waves back into the transducer element 16. These reflected ultrasound waves may interfere with forward-bound ultrasound waves of the transducer element 16 and may result in a poor image quality. Conversely, the unitary structure of the backing component 20 may not present any substantial intermediate reflection of the ultrasound waves within the backing component 20 and hence aid in attenuation of the ultrasound waves, resulting in enhanced image quality.

In some embodiments, an ultrasound probe 10 having an acoustic lens 12, an acoustic matching layer 14, a transducer element 16, and a backing component 20 is presented, as illustrated in FIG. 1. The backing component has a unitary structure of a first material and a second material and further has a variation in packing density of the first material across at least a portion of a thickness of the backing component. In some embodiments, the variation in packing density of the first material is in the form of a step change across the at least a portion of thickness of the backing component and in some other embodiments, the variation in packing density of the first material is continuous across the at least a portion of thickness of the backing component.

In some embodiments of the present disclosure, a method of making a backing component for a transducer element in an ultrasound probe is presented. The method includes performing an additive manufacturing technique using a first material and a second material to form the backing component comprising a unitary structure of the first material and the second material. Performing the additive manufacturing technique includes varying a packing density of the first material across at least a portion of thickness of the backing component.

"Additive manufacturing" is a term used herein to describe a process which involves layer-by-layer construction or additive fabrication (as opposed to material removal as with conventional machining processes). Such processes may also be referred to as "rapid manufacturing processes". The additive manufacturing process forms net or near-net shape structures through sequentially and repeatedly depositing and joining material layers. As used herein the term "near-net shape" means that the additively manufactured structure is formed very close to the final shape of the structure, not requiring significant traditional mechanical finishing techniques, such as machining or grinding following the additive manufacturing process. Additive manufacturing systems and methods include, for example, and without limitation, vat photopolymerization, powder bed fusion, binder jetting, material jetting, sheet lamination, material extrusion, directed energy deposition and hybrid systems. These systems and methods may include, for example, and without limitation, stereolithography; digital light processing; scan, spin, and selectively photocure; continuous liquid interface production; selective laser sintering; direct metal laser sintering; selective laser melting; electron beam melting; selective heat sintering; multi-jet fusion; smooth curvatures printing; multi-jet modeling; laminated object manufacture; selective deposition lamination; ultrasonic additive manufacturing; fused filament fabrication; fused deposition modeling; laser metal deposition; laser engineered net shaping; direct metal deposition; hybrid systems; and combinations of these methods and systems. These methods and systems may employ, for example, and without limitation, all forms of electromagnetic radiation, heating, sintering, melting, curing, binding, consolidating, pressing, embedding, and combinations thereof.

Additive manufacturing may be used to manufacture articles using computer aided design (CAD) models. Binder jet technique is a type of additive manufacturing technique capable of printing a metal, ceramic, or polymer part by selectively depositing a CAD-determined pattern of a binder solution (e.g., liquid glue) into a powder bed, overcoating with fresh particles, and repeating the depositing process until the part is complete. The printed part generally undergoes a curing process, which solidifies the binder solution within the powder to form a green body (e.g., as-printed, unfired) part. The green body part subsequently may undergo a debinding process, which is generally a heat treatment process that decomposes and removes the binder from the green body part, forming a brown (e.g., partially-fired) part. The brown body part may further undergo a sintering process to consolidate the powder and form a final (e.g., consolidated) part.

In some embodiments of the present disclosure, a modified binder jet process is used for making the backing component for a transducer element of the ultrasound probe. The method of making the backing component using the modified binder jet process includes fabricating a first build layer having a binder and consolidated particles of the first material. The consolidated particles of the first material in the first build layer are formed by applying a first force to the particles of the first material. The method further includes fabricating a second build layer on the first build layer, the second build layer having the binder and consolidated particles of the first material. The consolidated particles of the first material in the second build layer are formed by applying a second force to the particles of the first material. The first force is different from the second force. Therefore, effectively, the packing density of the first material in the first build layer as a result of consolidation using the first force is different from the packing density of the first material in the second build layer as a result of consolidation using the second force. In some embodiments, the consolidated particles of the first material in the first build layer are consolidated prior to, during, or after an addition of the binder in fabricating the first build layer. In some embodiments, the consolidated particles of the first material in the second build layer are consolidated prior to, during, or after an addition of the binder in fabricating the second build layer.

Figure 2A:
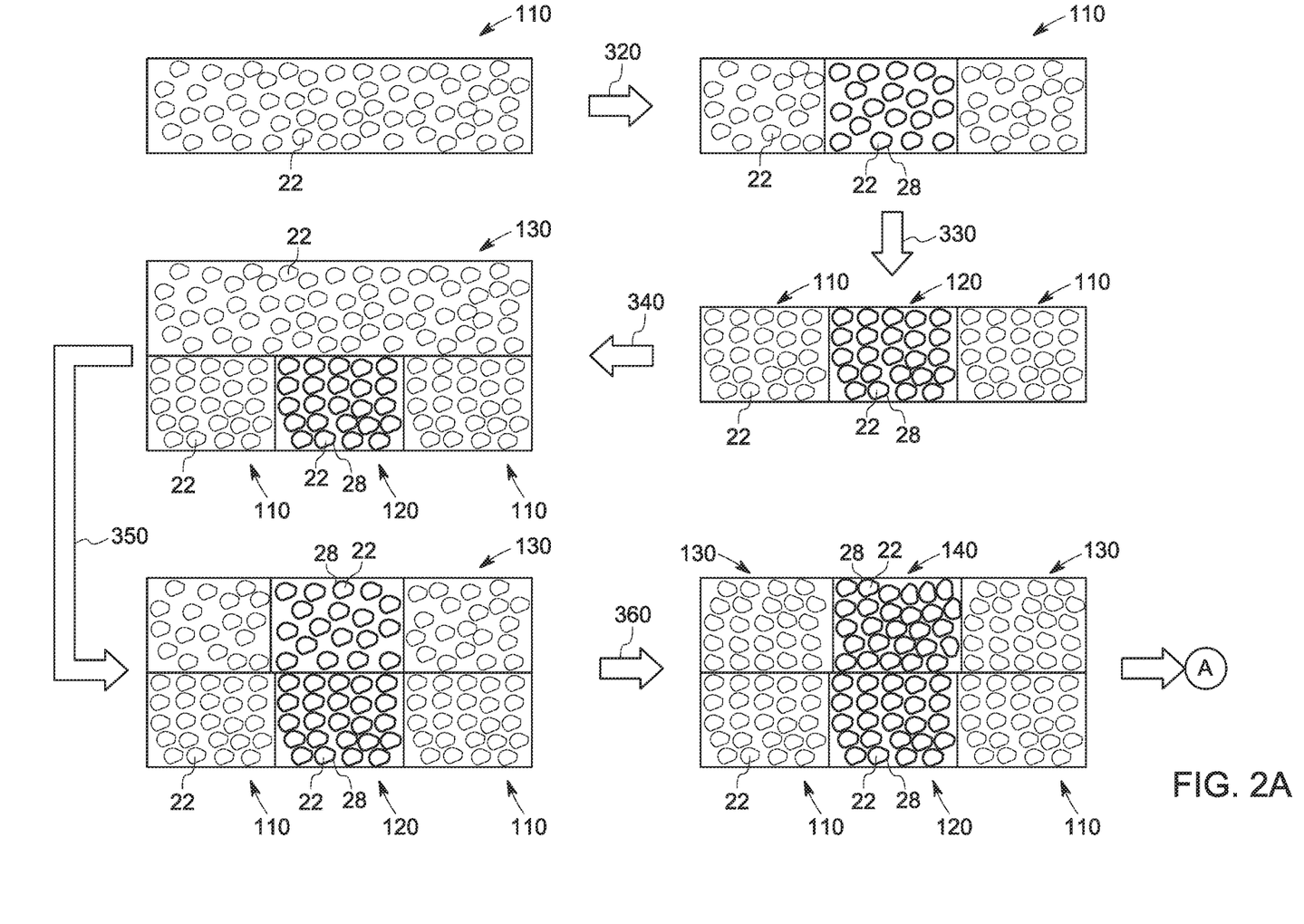
FIG. 2A is a schematic diagram illustrating some steps of making a backing component, in accordance with some embodiments of the present disclosure.
Figure 2B:
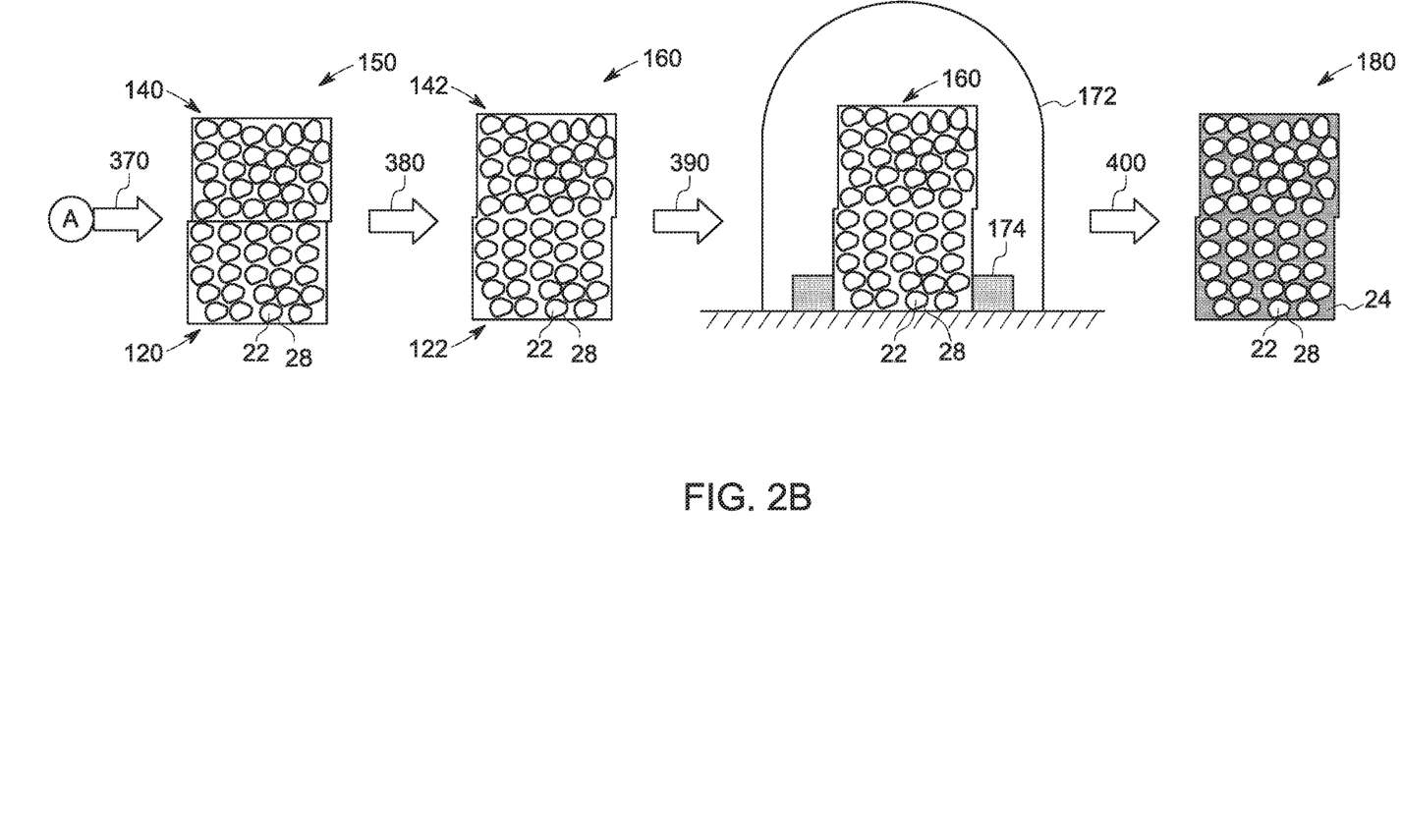
FIG. 2B is a schematic diagram illustrating some steps of making a backing component, in accordance with some embodiments of the present disclosure.
Figure 3:
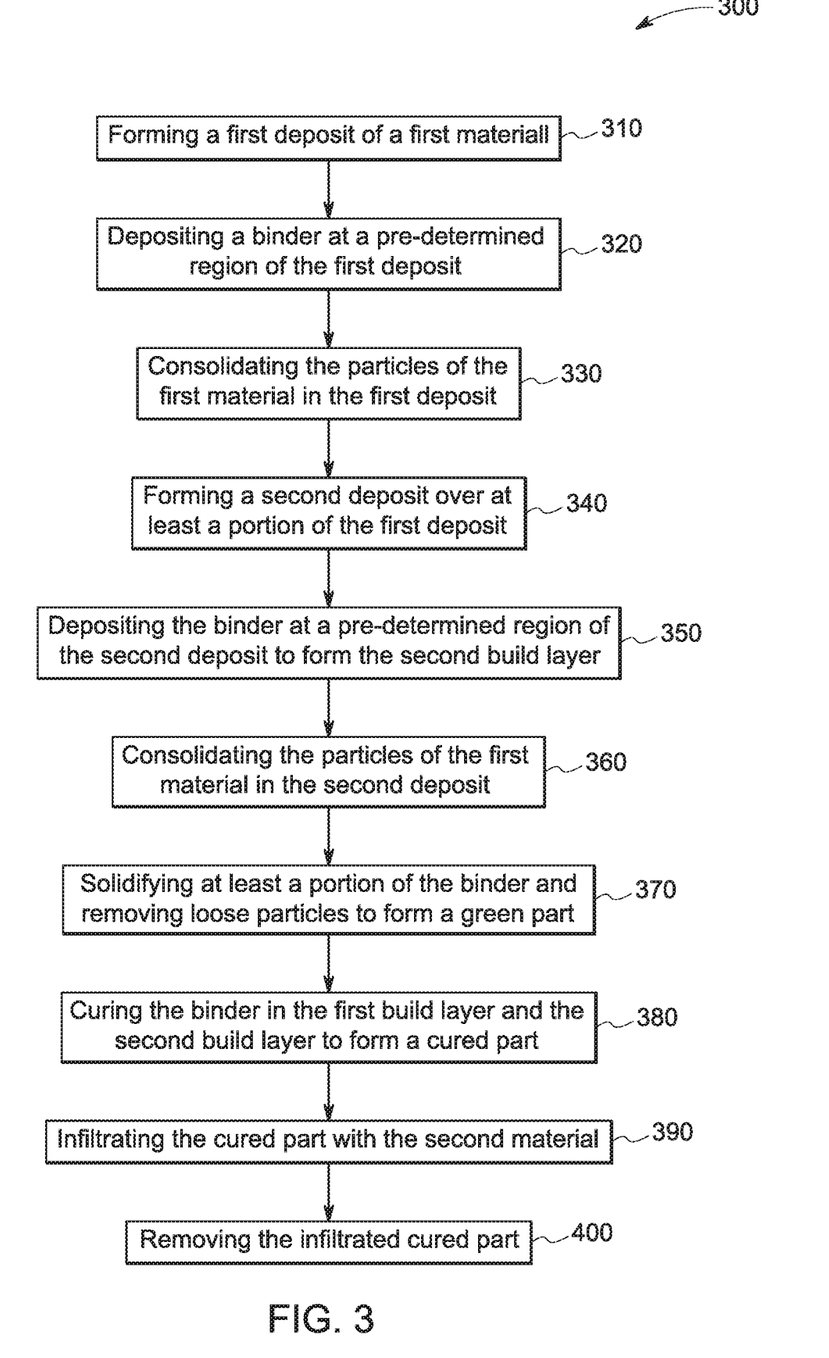
FIG. 3 is a flowchart of a method of making a backing component, in accordance with some embodiments of the present disclosure.

FIGS. 2A, 2B, and 3 illustrate an example method of making the backing component using the modified binder jet process discussed above. Initially, at block 310 (Not shown in FIG. 2A or 2B), a first deposit 110 of particles of the first material 22 is formed. At block 320, a binder 28 is deposited on a selected, pre-determined region of the first deposit 110 to impregnate at least a portion of the first deposit 110. The binder 28 coats at least some of the particles of the first material 22 in the pre-determined region of the first deposit 110 and provides cohesion between the particles. At block 330, some of the particles of the first material 22 in the first deposit 110 are consolidated by applying a first force, thereby forming the first build layer 120 in the pre-determined region of the first deposit 110. Thus, in some embodiments, the first deposit 110 includes the first build layer 120 after the addition of the binder 28 and consolidation of the particles of the first material 22. The consolidated particles of the first material 22 in the first build layer 120 are bonded together by the binder 28, while the particles in the remaining portions of the first deposit 110 are loosely packed, in the absence of any binder. In some embodiments, the binder may be deposited as a solid, liquid, or melt. In some embodiments, the binder may be deposited in a solution form.

In the example of FIGS. 2A and 3, at block, 340, a second deposit 130 of particles of the first material 22 is formed over at least a portion of the first deposit 110, including, over at least a portion of the first build layer 120. At block 350, the binder 28 is deposited at a pre-determined region of the second deposit 130. The binder 28 interpenetrates at least a portion of the second deposit 130 coating at least some particles of the first material 22. At block 360, the particles of the first material 22 in the pre-determined region of the second deposit 130 are consolidated by applying a second force to form a second build layer 140 at the pre-determined region of the second deposit 130. The second build layer 140 at least partially overlaps the first build layer 120. The overlapping of the first build layer and the second build layer 140 may be varied according to the shape and size of the desired backing component. At block 370, at least a portion of the binder 28 in the first build layer 120 and the second build layer 140 is solidified and loose powders are removed to form a green part 150. In some embodiments, the binder 28 provides a cohesion between the first build layer 120 and the second build layer 140.

The binder 28 may be any binder compatible with the first material 22. Suitable binders include, but are not limited, to thermoplastic resins (e.g., polyethylene, polypropylene, polyvinyl chloride, polycarbonate, and/or ethylene copolymers), thermoset resins (e.g., polyurethane, phenolic, polyimide, polyester, melamine, epoxy, polycyanurate), or combinations thereof. In some embodiments, the binder 28 may be dissolved in a solvent to form the binder solution before disposing on the first deposit 110. Suitable solvents include but are not limited to 2-pyrrolidone, methanol, isopropyl alcohol, water, 1,5-pentanediol, ethylene glycol, triethylene glycol, or combinations thereof. While a same binder 28 is used for binding the first material 22 in the first build layer 120 and in the second build layer 140 in this example embodiment, the first build layer 120 and the second build layer 140 may be formed by using two different binders in other embodiments.

According to the embodiments of the modified binder jet process, a first force is applied to the first deposit 110 and a second force is applied to the second deposit 130 to consolidate the first deposit 110 and the second deposit 130, especially to consolidate the particles of the first material in the pre-determined regions of the first deposit 110 and second deposit 130. Thus, the consolidated particles of the first material present in the first build layer 120 are consolidated by the first force and the consolidated particles of the first material in the second build layer 140 are consolidated by the second force. In some embodiments, a value of the first force applied to the first deposit 110 is different from the value of the second force applied to the second deposit 130. The first force may be applied to the first deposit 110 prior to, during, or after the addition of the binder 28 to the first material 22, before the deposition of the second deposit 130. In some embodiments, the first force is applied to the first deposit 110 before the addition of the binder 28 to consolidate the first deposit 110 and control the amount of binder 28 impregnated in the first build layer 120. In some embodiments, the first force is applied to the first deposit 110 during the addition of the binder 28. In some embodiments, the first force is applied to the first deposit 110 after the addition of the binder 28. In some specific embodiments, the first force is continuously applied to the first deposit before, during, and after the addition of the binder 28. The second force may be applied to the second deposit 130 prior to, during, or after the addition of the binder 28 to the first material 22. In some embodiments, the second force is applied to the second deposit 130 before the addition of the binder 28. In some embodiments, the second force is applied to the second deposit 130 during the addition of the binder 28. In some embodiments, the second force is applied to the second deposit 130 after the addition of the binder 28. In certain embodiments, the second force is continuously applied to the second deposit before, during, and after the addition of the binder 28.

Techniques for applying force for consolidation of the first deposit 110 and the second deposit 130 include, but are not limited to vibrating, compacting, solutionizing, aging, or combinations thereof. In some embodiments, the consolidation includes vibrating the first material 22 during the deposition of the first deposit 110. In some embodiments, the first deposit is pressed to compact the particles of the first material 22, after the formation of the first deposit 110 and before the deposition of the second deposit 130. The packing density of the first material 22 in the first build layer 120 depends on the first force applied in consolidating the first deposit 110. In some embodiments, the pre-determined region of the first deposit 110 is selectively consolidated to have a particular packing density of the first material 22 in the first build layer 120, regardless of the force applied to the rest of the first deposit 110. In some embodiments, the first force applied to the first deposit 110 is directly proportional to the required packing density of the first material 22 in the first build layer 120. In some embodiments, the first build layer 120 may be formed by applying hot isostatic pressing (HIP) to the first deposit 110. Specific hot isostatic pressing conditions are dependent on the materials of the first material 22.

The method of consolidating the first material in the second deposit 130 may be similar to or different from the method used for consolidating the first deposit 110. In some embodiments, by effectively varying the force applied for consolidating the first deposit 110 and the second deposit 130, the packing density of the first material in the second build layer 140 may be varied with respect to the packing density of the first material in the first build layer 120.

In some embodiments, a thickness of the first deposit 110 may be different from a thickness of the second deposit 130. A difference in thickness of the two deposits may result in a difference in the degree of consolidation of the particles of the first material in the respective two build layers, even in the event of applying the same amount force for consolidating the first deposit 110 and the second deposit 130.

In some embodiments, the particles of the first material 22 in the second deposit 130 are consolidated using a different consolidating technique compared to the technique used for consolidating the particles of the first material 22 in the first deposit 110, resulting in different respective packing densities of the first material 22 in build layers 120 and 140. In some embodiments, depending on the technique applied for consolidating the second deposit 130, the particles of the first material 22 in the first build layer 120 may further be consolidated during the consolidation of the second deposit 130. However, the technique of consolidation and the force applied are controlled to result in a dissimilar packing density of the first material 22 in the first build layer 120 as compared to the packing density of the first material 22 in the second build layer 140. Therefore, by using one or more of the afore-mentioned techniques, the packing density of the first material 22 across at least a portion of the thickness of the backing component may be varied.

Referring to FIGS. 2B and 3, at block 370, the binder may be solidified to bind the first build layer 120 to the second build layer 140 in the respective overlapping portions of the first build layer 120 and the second build layer 140 and the loose particles may be removed to form the green part 150. In some embodiments, the binder may be at least partially cured by heating (e.g., microwave and/or thermal) or by the application of actinic radiation (e.g. visible light, and/or ultraviolet light). Additional deposits of particles of the first material 22 and further build layers are formed in order to form a green part 150 having the required size and shape. In some embodiments, the binder of the green part 150 may be at least partially cured sequentially as the build layers are formed. In some embodiments, the binder of the green part 150 may be at least partially cured after formation of the multiple build layers. In some embodiments, the method includes forming at least 10 build layers. In some embodiments, the method includes forming at least 100 build layers. In certain embodiments, the method includes forming at least 1000 build layers to make the green part 150. By varying the force applied on the particles of the first material 22 in each of the successive deposits, packing density of the first material 22 in each of the formed build layers may be varied, thereby resulting in variation of the packing density of the first material 22 across at least a portion 26 of the thickness of the backing component. For example, by gradually increasing the force applied on the particles of the first material 22 in successive deposits, successive build layers having increasing packing density of the first material 22 may be formed. The force applied may be gradually increased while forming few successive build layers and then gradually decreased while forming next few successive build layers to have a gradual increase and then gradual decrease in packing density of the first material 22 across the portion 26.

With continued reference to FIGS. 2B and 3, in some embodiments, the green part 150 may further be densified by curing at block 380 to form a cured part 160 having a cured first build layer 122 and a cured second build layer 142. Substantially fully curing the binder of the green part 150 allows for the green part 150 to be more easily physically manipulated during further processing without damage to the green part or a final component. Curing may enhance the mechanical, optical, and/or electrical properties of the green part 150, including, but not limited to, hardness, fracture toughness, bending strength, abrasion resistance, thermal expansion, thermal conductivity, thermal shock resistance, thermal shock cycling, or combinations thereof. Curing may also diminish boundaries of the build layers, if any present, and form the unitary structure of the cured first build layer 122 and the cured second build layer 142.

The second material 24 may be incorporated into the backing component before, during, or after curing of the binders in the green part 150. In some embodiments, the second material 24 is impregnated into the cured first build layer 122 and the cured second build layer 142 of the cured part 160 as discussed in block 390. In some embodiments, the second material 24 is impregnated into the cured part 160 through infiltration. Infiltration may be performed by various methods known in the art, including, but not limited to pressure assisted infiltration, vacuum driven infiltration, capillarity driven infiltration, or combinations thereof. In some embodiments, a capillary driven infiltration method is used to infiltrate the cured part 160 to form infiltrated cured part 180. In some embodiments, the capillary driven infiltration may further be aided by vacuum by conducting infiltration inside a vacuum chamber 172, as shown in FIG. 2. Depending on the material characteristics of the second material 24, a melt, a solution, or a precursor solution 174 of the second material 24 may be used for the infiltration. The infiltrated cured part 180 may be removed from the vacuum chamber 172 at block 400 to form the backing component 20 (FIG. 1).

In some embodiments, the above-described method provides a near net shape backing component with a variation in the packing density of the first material 22 and the second material 24 across at least a portion of the thickness of the backing component. Near net shape components are formed in the manufacturing process substantially in the shape and configuration desired for use. Near net shape manufacturing may be used produce components having curved surfaces and complex geometries. Components manufactured to near net shape typically require little or no post fabrication processing (e.g., machining) prior to use, allowing material loss and/or wastage due to post fabrication processing to be reduced or eliminated.

The packing density of the first material 22 and the second material 24 in the backing component 20 formed by the method disclosed herein may be designed to vary in a stepwise manner or in a continuous manner across at least the portion of the thickness of the backing component. In some embodiments, the method is used to vary the packing density of the first material and the second material such that the packing density of the first material increases across a first portion of the thickness and decreases across a second portion of the thickness, while the packing density of the second material decreases across the first portion of the thickness and increases across the second portion of the thickness.

In the embodiments of the method described above, the cured binder acts as a matrix material for the first material 22 and the second material 24 in the formed infiltrated cured part 180. The backing component described in accordance with some embodiments of the present disclosure does not involve any high temperature treatment steps, and hence, may be directly formed over the transducer element without harming the transducer element. In some embodiments, electrical connections to the transducer element can also be assembled by performing the exemplary additive fabricating techniques disclosed herein directly on the transducer element. In some other embodiments, the backing component may be formed separately and attached to the transducer element.

In some embodiments, the cured part 160 may be pre-sintered at a temperature less than 400° C. to remove the binder before infiltration of the second material, such that the final backing component is free of the binder. Further, in some embodiments, depending on the characteristics of the second material, a further drying, curing, pre-sintering, or sintering step may be carried out after infiltration, to obtain the final backing component.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

The invention claimed is:

1. A backing component configured to receive and attenuate transmitted acoustic signals from a transducer element in an ultrasound probe, the backing component comprising:
   a unitary structure of a first material and a second material, and a variation in packing density of the first material across at least a portion of a thickness of the backing component.

2. The backing component of claim 1, wherein the variation in packing density of the first material is in the form of a step change across the at least a portion of thickness of the backing component.

3. The backing component of claim 1, wherein the variation in packing density of the first material is continuous across the at least a portion of thickness of the backing component.

4. The backing component of claim 1, further comprising a variation in packing density of the second material across the at least a portion of the thickness of the backing component.

5. The backing component of claim 1, wherein the first material comprises a metal material and the second material comprises a polymer material.

6. The backing component of claim 5, wherein the metal material comprises tungsten.

7. The backing component of claim 5, wherein the polymer material comprises an epoxy polymer.

8. An ultrasound probe comprising the backing component of claim 1, wherein the thickness of the backing component is defined in a direction parallel to a Z-axis of the ultrasound probe.

9. The backing component of claim 1, wherein:
the first material is a mixture of two or more materials.

10. The backing component of claim 1, wherein:
the first material has a particle size between 10 micrometers and 50 micrometers.

11. The backing component of claim 1, further comprising:
a matrix material that is different from the first material and the second material, the matrix material bonding the first material to the second material.

12. The backing component of claim 1, wherein:
the packing density of the first material increases or decreases progressively across a thickness of the backing component.

13. The backing component of claim 1, wherein:
wherein the variation in packing density of the first material is in the form of a plurality of step changes across the at least a portion of thickness of the backing component;
wherein each step change of the plurality of step changes contributes less than about 0.2% of the total variation in packing density of the first material across the at least a portion of thickness of the backing component.

14. The backing component of claim 1, wherein:
the variation in packing density of the first material is in the form of a step change across a first portion of the thickness of the backing component and is continuous across a second portion of the thickness of the backing component.

15. The backing component of claim 1, wherein:
the backing layer is manufactured through an additive manufacturing process.

16. An ultrasound probe comprising an acoustic lens, an acoustic matching layer, a transducer element, and a backing component, the backing component comprising:
a unitary structure of a first material and a second material, and a variation in packing density of the first material across at least a portion of a thickness of the backing component.

17. The ultrasound probe of claim 16, wherein the variation in packing density of the first material is in the form of a step change across the at least a portion of thickness of the backing component.

18. The ultrasound probe of claim 16, wherein the variation in packing density of the first material is continuous across the at least a portion of thickness of the backing component.

* * * * *